United States Patent

Fukasawa et al.

Patent Number: 4,791,140
Date of Patent: Dec. 13, 1988

[54] METHOD OF PREVENTING CRAZING OF COSMETICS

[75] Inventors: Junichi Fukasawa, Yokohama; Yoshimitsu Ina, Funabashi; Hisao Tsutsumi, Miyashiromachi, all of Japan

[73] Assignee: Kao Corporation, Tokyo, Japan

[21] Appl. No.: 855,725

[22] Filed: Apr. 25, 1986

[30] Foreign Application Priority Data

May 7, 1985 [JP] Japan ................................ 60-96343

[51] Int. Cl.$^4$ .................... A61K 7/021; A61K 7/025; A61K 7/031
[52] U.S. Cl. ...................................... 514/845; 424/63; 514/846; 514/847; 514/944; 514/969
[58] Field of Search ....................... 514/944, 845, 847; 424/63, 969; 106/287.17, 304, 308 Q

[56] References Cited

U.S. PATENT DOCUMENTS

| | | | |
|---|---|---|---|
| 3,757,864 | 9/1973 | Crawford et al. | 166/308 |
| 4,140,656 | 2/1979 | Mast | 514/944 |

OTHER PUBLICATIONS

Whateley, Chem. Abs., 1967, vol. 66, p. 22581e.
Sato et al, Chem. Abs., 1975, vol. 83, p. 187601a.
Johnson, Chem. Abs., 19, vol. 61, p. 8339.
Karpachera, Chem. Abs., 1969, vol. 71, p. 7016j.
Yamada, Chem. Abs., 1979, vol. 91, 5926v.
Nishibata et al, 1980, vol. 92, p. 60149q.

Primary Examiner—Dale R. Ore
Attorney, Agent, or Firm—Oblon, Fisher, Spivak, McClelland & Maier

[57] ABSTRACT

A novel cosmetic comprises an oil gel formed by at least one metal salt of a dialkyl phosphate of the following general formula (I), (II) or (III)

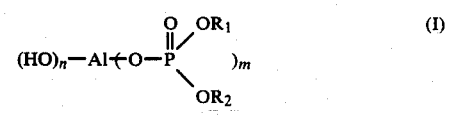

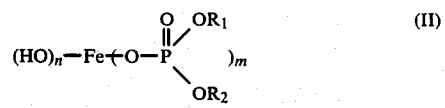

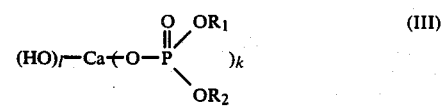

in which each $R_1$ and each $R_2$ independently represent a saturated or unsaturated, linear or branched hydrocarbon group having from 8 to 36 carbon atoms, m is an integer of from 1 to 3, n is an integer of from 0 to 2, k is a value of 1 or 2, and l is a value of 0 to 1, and a cosmetic oil.

The metal salt of the dialkyl phosphate can yield a good oil gel when it is incorporated into the oil in an amount as small as 0.1 to 10% of the oil. Further, the dialkyl phosphate retains good feel of oils without causing oozing of the oil, crazing, discoloration, perspiration and the like.

4 Claims, No Drawings

METHOD OF PREVENTING CRAZING OF COSMETICS

BACKGROUND OF THE INVENTION

(1) Field of the Invention

This invention relates to cosmetics comprising, as an oil gelling agent, metal salts of dialkyl phosphates having a good oil gelling characteristic.

(2) Description of the Prior Art

As is known in the art, metallic soaps and dextrin fatty acid esters have been used as gelling agents, W/O emulsion stabilizers and pigment dispersants due to the good oil gelling ability.

Among these oil gelling agents for cosmetics, however, metallic soaps are disadvantageous in that they require elevated temperatures near 100° C. in order to dissolve liquid fats and oils therein, thus inviting a lowering in quality of oils on preparation of cosmetics and discoloration of pigments. When metallic soaps are used to gel oils for cosmetics, there are disadvantages in that the oil oozes with time and the cosmetics are crazed, causing the cosmetics to perspirate with a lowering of the quality. Moreover, since the feel of an oil for cosmetics to the touch is an important factor on feels, such as fitness or affinity for skin, spreading and gloss, of cosmetic articles, the amount of an oil gelling agent should preferably be as small as possible in order not to cause the lowering of the feel. However, when the amount of a metallic soap is less than 10 wt% of an oil (hereinafter referred simply as %), the oozing of the oil with time and the crazing take place to greater extents.

On the other hand, dextrin fatty acid esters cannot impart satisfactory gel strength and shape retention, coupled with the disadvantage in that when the esters are added to cosmetics, any gelling effect cannot be obtained.

Accordingly, there is a demand of development of an oil gelling agent which ensures a stable oil retention with time and a good shape retention and has a temperature of dissolution in oil lower than an ordinary emulsification temperature when it is added in small amounts not lowering the feel of an oil, preferably in amounts not larger than 10% of the oil.

SUMMARY OF THE INVENTION

Under these circumstances in the art, the present inventors made intensive studies and, as a result, found that a specific type of metal salt of dialkyl phosphate serves as an oil gelling agent which satisfies the above requirement and can yield a good oil gel on addition in an amount as small as 0.1 to 10%. In addition, when the metal salt is added, good feel of oils cannot be lost without causing oozing of the oil, crazing, discoloration, perspiration and the like. Thus, good cosmetics can be obtained. The present invention is accomplished based on the above finding.

More particularly, the present invention provides cosmetics which comprise an oil gel formed by at least one metal salt of a dialkyl phosphate of the following general formula (I), (II) or (III)

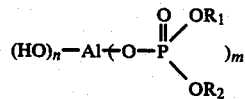 (I)

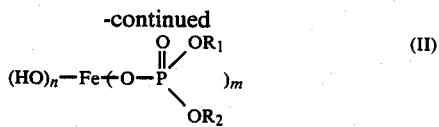 (II)

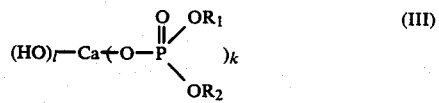 (III)

in which each $R_1$ and each $R_2$ independently represent a saturated or unsaturated, linear or branched hydrocarbon group having from 8 to 36 carbon atoms, m is an integer of from 1 to 3, n is an integer of from 0 to 2, k is 1 or 2, and l is 0 or 1, and an oil for cosmetics.

DETAILED DESCRIPTION OF THE INVENTION AND PREFERRED EMBODIMENTS

The metal salts of dialkyl phosphates are known compounds, but have been heretofore used only as water repellents in the field of fibers. The application to cosmetics has never been known.

The hydrocarbon groups represented by $R_1$ and $R_2$ of the formulae (I) to (III) are those groups having from 8 to 36 carbon atoms, preferably from 12 to 22 carbon atoms. The hydrocarbon groups having a smaller number of carbon atoms cannot impart a satisfactory gel strength to oils and fats. Examples of the hydrocarbon groups include octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, octenyl, nonenyl, decenyl, dodecenyl, undecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, pentacocenyl, hexacocenyl, heptacocenyl, octacocenyl, nonacocenyl, triacontenyl, hentriacontenyl, dotriacontenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacasadienyl, hexacosadienyl, heptacosadienyl, octacosadienyl, nonacosadienyl, triacontadienyl, hentriacontadienyl, dotriacontadienyl, 2-hexyldecyl, 2-octylundecyl, 2-decyltetradecyl, 2-undecylhexadecyl, 2-tetradecyloctadecyl and the like.

The aluminum salts of dialkyl phosphates of the formula (I) can be obtained, for example, by a method (1) in which aluminum salts such as aluminum chloride, ammonium sulfate, aluminum nitrate, aluminum phosphate, aluminum carbonate and the like, dialkyl phosphates such as sodium dialkyl phosphates, potassium dialkyl phosphates, triethanolamine dialkyl phosphates, alginine dialkyl phosphates and the like and, if necessary, alkali hydroxides are reacted in an aqueous solution under heating conditions, if necessary, thereby effecting the salt exchange, and by a method (2) in which aluminum alcoholates such as aluminum isopropylate, aluminum sec-butyrate, mono-sec-butoxyaluminum diisopropylate and the like and dialkyl phosphates are reacted in a non-aqueous solvent under heating conditions, followed by hydrolysis, if necessary.

Because of the formation of the salts having a high gelling ability, the latter method is preferred.

The iron dialkyl phosphates of the general formula (II) are obtained by reacting iron salts such as ferric chloride, ferric sulfate, ferric nitrate, ferric phosphate, ferric carbonate and the like, dialkyl phosphates such as sodium dialkyl phosphates, potassium dialkyl phosphates, triethanolamine dialkyl phosphates, alginine dialkyl phosphates and the like and, if necessary, alkali hydroxides in an aqueous solution under heating conditions, if necessary, thereby effecting the salt exchange.

The calcium dialkyl phosphates of the formula (III) is obtained by a method in which there are reacted calcium salts such as calcium chloride, calcium sulfate, calcium nitrate, calcium phosphate, calcium carbonate and the like, dialkyl phosphates such as sodium dialkyl phosphates, potassium dialkyl phosphates, triethanolamine dialkyl phosphates, alginine dialkyl phosphates and the like and, if necessary, alkali hydroxides in an aqueous solution under heating conditions, if necessary, thereby effecting salt exchange.

The oils for cosmetics which are another essential ingredient of the cosmetics of the present invention may include non-polar liquid oils such as linear or branched hydrocarbons (whichever saturated or unsaturated), and synthetic ester oils such as of higher alcohols and fatty acids. These oils may be used singly or in combination. Of these essential cosmetic oils, non-polar liquid oils such as liquid paraffin, squalane and the like exhibit high gel strength, oil retention and shape retention on addition of metal salts of dialkyl phosphates. Throughout the specification, these essential cosmetic oils may be referred to simply as a "cosmetic oil".

For the preparation of the cosmetics of the present invention, ordinarily used arbitrary additives other than the essential metal salts of dialkyl phosphates and cosmetic oils may be added including other types of oils, purified water, various surface active agents, humectants, preservatives, antioxidants, perfumes, powders and the like. Other oils include higher alcohols, higher fatty acids, waxes and the like. When these oil additives are added, the gel strength, oil retention and shape retention can be arbitrarily controlled.

The surface active agents include polyoxyethylene alkyl ethers, polyoxyethylene/fatty acid esters, polyoxyethylene/sorbitan/fatty acid esters, sorbitan/fatty acid esters, glycerin/fatty acid esters, polyoxyethylene hardened caster oil, polyoxyethylene/sorbitol/fatty acid esters and the like; the humectants include sorbitol, glycerine, propylene glycol, 1,3-butylene glycol, lactic acid, sodium lactate, polyethylene glycol and the like; the preservatives include alkyl para-oxybenzoates, sodium benzoate, potassium sorbates, phenoxy ethanol and the like; the antioxidants include tocopherol, sesamol, sesamolin, lecithin and the like; and the powders include titanium oxide, zinc oxide, ultramarine, chromium oxide, iron oxide, talc, sericite, mica, kaolin, titanium dioxide-coated mica, iron oxide-coated mica, organic pigments and the like.

The amount of the metal dialkyl phosphates in the cosmetics of the invention is generally in the range of 0.1 to 30% of the cosmetic oil. Larger amounts are unfavorable because the good properties of a gelling agent or oil (spreading, gloss, fitness and the like) lower. Smaller amounts are also unfavorable because the effects of the metal salts are not shown. In order to make the best use of the favorable feel of cosmetic oils, the amount preferably ranges from 0.1 to 10%. The amount of the cosmetic oil to be incorporated in the cosmetics of the invention depends on the type of the cosmetics, and may be such an amount that would be used in ordinary cosmetic compositions.

The cosmetics of the invention are prepared by mixing under heating conditions the essential ingredients of a metal dialkyl phosphate and a cosmetic oil and optional ingredients, for example, by the use of a homomixer, a homodisper, a three-roll mixer or the like, and shaping the mixture into a desired form, if necessary. The cosmetics of the invention can be prepared into makeup cosmetics such as foundations, rouges and the like, and skin care cosmetics such as creams, oil gel cleansing creams and the like.

The present invention is more particularly described by way of references, which refer to preparation of metal alkyl phosphates, and examples.

Reference 1

Aluminium tris(dicetyl phosphate):

500 ml of ethanol was placed in a 3 liter beaker, to which 100 g (0.183 mol) of dicetyl phosphate (acid value: 103.0, molecular weight: 546) was added at 60° to 70° C. After the addition, the mixture was agitated for about 30 minutes, after which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hour. 500 ml of water was placed in a 3 liter beaker, to which the above reaction mixture was added, followed by dissolution at 70° to 75° C. for 30 minutes under agitation. Thereafter, 98.2 g ($AlCl_3$: 0.061 mol) of a 15% $AlCl_3.6H_2O$ solution was added, followed by salt exchange at 70° to 75° C. for 1 hour. After completion of the salt exchange, the reaction mixture was filtered, washed twice with each 500 ml of water and once with 500 ml of acetone, followed by drying at 60° C. for 30 hours to obtain 100 g of aluminum tris(dicetyl phosphate) in the form of white powder.

Found:
content of phosphorus 5.4%,
content of aluminum 1.6%.
Calculated:
content of phosphorus 5.6%,
content of aluminum 1.6%.

Reference 2

Aluminum tris(dicetyl phosphate):

15 g (0.027 mol) of dicetyl phosphate (acid value: 103.0, molecular weight: 546) and 1.87 g (0.009 mol) of aluminum isopropoxide were added to 70 ml of completely dehydrate benzene, followed by mounting the Widmer distillation device and heating on an oil bath at 110° C. for dissolution, whereupon the isopropanol was distilled at 72° C. and the benzene was distilled at 80° C. The remaining benzene was distilled off under reduced pressure to obtain 15 g of aluminum tris(dicetyl phosphate) in the form of white powder.

Found:
content of phosphorus 5.6%,
content of aluminum 1.6%.
Calculated:
content of phosphorus 5.6%,
content of aluminum 1.6%.

Reference 3

Aluminum bis(dicetyl phosphate):

500 ml of ethanol was palced in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above rection product was added, followed by dissolution at 70° to 75° C. for 30 minutes under agitation. To the solution were added 147.3 g ($AlCl_3$: 0.092 mol) of an aqueous 15% $AlCl_3.6H_2O$ solution and 36.65 g (NaOH: 0.092 mol) of a 10% NaOH solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of aluminum bis(dicetyl phosphate) as white powder.

Found:
content of phosphorus 5.3%,
content of aluminum 2.3%.
Calculated:
content of phosphorus 5.5%,
content of aluminum 2.4%.

Reference 4

Aluminum mono(dicetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution were added 294.6 g ($AlCl_3$: 0.183 mol) of an aqueous 15% $AlCl_3.6H_2O$ solution and 146.6 g (NaOH: 0.368 mol) of a 10% NaOH solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of aluminum mono(dicetyl phosphate) as white powder.

Found:
content of phosphorus 5.0%,
content of aluminum 4.4%.
Calculated:
content of phosphorus 5.1%,
content of aluminum 4.5%.

Reference 5

Calcium bis(diacetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution was added 68 g ($CaCl_2$: 0.092 mol) of an aqueous 15% $CaCl_2$ solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of calcium bis(dicetyl phosphate) as white powder.

Found:
content of phosphorus 5.5%,
content of calcium 3.4%.
Calculated:
content of phosphorus 5.5%,
content of calcium 3.5%.

Reference 6

Calcium mono(diacetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution were added 136 g ($CaCl_2$: 0.183 mol) of an aqueous 15% $CaCl_2$ solution and 73.3 g (NaOH: 0.183 mol) of a 10% NaOH solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of calcium mono(dicetyl phosphate) as white powder.

Found:
content of phosphorus 10.2%,
content of calcium 6.6%.
Calculated:
content o phosphorus 10.3%,
content of calcium 6.7%.

Reference 7

Iron tris(dicetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution was added 164 g ($Fe(NO_3)_3$: 0.061 mol) of an aqueous 15% $Fe(NO_3)_3.9H_2O$ solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of iron mono(dicetyl phosphate) as white powder.

Found:
content of phosphorus 5.5%,
content of iron 3.2%.
Calculated:
content of phosphorus 5.5%,
content of iron 3.3%.

Reference 8

Iron bis(dicetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitatd for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution were added 246 g (Fe(NO$_3$)$_3$: 0.092 mol) of an aqueous 15% Fe(NO$_3$)$_3$.9H$_2$O solution and 36.65 g (NaOH: 0.092 mol) of a 10% NaOH solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of iron bis(dicetyl phosphate) as white powder.

Found:
content of phosphorus 5.2%,
content of iron 4.8%.
Calculated:
content of phosphorus 5.3%,
content of iron 4.8%.

Reference 9

Iron mono(dicetyl phosphate):

500 ml of ethanol was placed in a 3 liter beaker, to which 100 g (0.183 mol) of dicetyl phosphate (acid value: 103.0, molecular weight 546) was added at 60° to 70° C. After the addition, the mixture was agitated for 30 minutes, into which 73.3 g (NaOH: 0.183 mol) of a 10% NaOH solution was dropped in 30 minutes at 60° C., followed by agitation for reaction at 60° to 65° C. for 30 minutes. After cooling to 30° C., the reaction mixture was filtered and dried at 60° C. for 10 hours. 500 ml of water was placed in a 3 liter beaker, to which the above reaction product was added, followed by dissolution at 70° to 75° C. for 30 minutes under agitation. To the solution were added 492 g (Fe(NO$_3$)$_3$: 0.183 mol) of an aqueous 15% Fe(NO$_3$)$_3$.9H$_2$O solution and 146.6 g (NaOH: 0.368 mol) of a 10% NaOH solution in order to conduct the salt exchange at 70° to 75° C. for 1 hour. After completion of the salt exchange, the reaction mixture was filtered, washed twice with each 500 ml of water and once with 500 ml of acetone, and dried at 60° C. for 30 hours to obtain 100 g of iron mono(dicetyl phosphate) as white powder.

Found:
content of phosphorus 4.8%,
content of iron 8.8%.
Calculated:
content of phosphorus 4.8%,
content of iron 8.8%.

EXAMPLE 1 n-Hexadecane was provided as an oil, to which various metal dialkyl phosphates prepared in References or in the same manner as in References were added in an amount of 1% based on the oil. Thereafter, a gelling temperature (i.e. the lowest temperature for forming a gel), a strength of the respective oil gels obtained by heating them to temperatures higher than the gelling temperature and cooling to 25° C., and an oil retention force were determined. For comparison, a metallic soap (aluminum distearate) and dextrin palmitate were used.

Gel Strength:

Determined by the use of the Rheometer, made by Fudo Ind. Co., Ltd. Oil Retention Force:

Each sample was allowed to stand at 25° C. for 2 days after gelling and the weight of the oozed oil was measured. This weight to the total weight was expressed as a syneresis rate by wt%.

The results are shown in Table 1.

TABLE 1

| Gelling Agent | Gelling Temperature (°C.) | Gel Strength (g/cm$^2$) | Syneresis Rate (%) |
|---|---|---|---|
| Inventive Products | | | |
| Aluminum tris(dicetyl phosphate) of Reference 1 | 60 | 42 | 0 |
| Aluminum tris(dicetyl phosphate) of Reference 2 | 59 | 50 | 0 |
| Aluminum tris(distearyl phosphate) prepared in the same manner as in Reference 1 | 66 | 86 | 0 |
| Aluminum tris(distearyl phosphate) prepared in the same manner as in Reference 2 | 66 | 90 | 0 |
| Aluminum bis(dicetyl phosphate) of Reference 3 | 50 | 15 | 0 |
| Aluminum mono(dicetyl phosphate) of Reference 4 | 40 | 15 | 0 |
| Calcium bis(dicetyl phosphate) of Reference 5 | 77 | 90 | 0 |
| Calcium mono(dicetyl phosphate) of Reference 6 | 65 | 20 | 0 |
| Iron tris(dicetyl phosphate) of Reference 7 | 63 | 42 | 0 |
| Iron bis(dicetyl phosphate) of Reference 8 | 50 | 10 | 0 |
| Iron mono(dicetyl phosphate) of Reference 9 | 42 | 10 | 0 |
| Comparative Products | | | |
| Aluminum distearate | 98 | 2 | 70 |
| Dextrin palmitate | 81 | — | — |

As will be seen from the above results, the gelling agents used in the present invention have low gelling temperatures and satisfactory gel strengths. When these agents are used as cosmetics, the oozing or exudation of oils which is an important factor from the standpoint of quality control has not been observed.

EXAMPLE 2

Oil Foundation:

Oil gelling agents used were aluminum tris(distearyl phosphate) (inventive product) and aluminum distearate for comparison. Oil foundations of the following formulations were prepared and subjected to a comparison test with respect to appearance.

Formulation:

| | | |
|---|---|---|
| (1) | Gelling agent | 0.7% |
| (2) | Liquid paraffin | 37.5 |
| (3) | Lanolin | 12.0 |
| (4) | Isopropyl myristate | 25.0 |
| (5) | Beeswax | 9.0 |
| (6) | Vaseline | 8.0 |
| (7) | Titanium oxide | 5.0 |
| (8) | Red iron oxide | 1.0 |
| (9) | Yellow iron oxide | 1.0 |
| (10) | Black iron oxide | 0.4 |
| (11) | Perfume | 0.4 |
| | Total | 100 |

Preparation:
The gelling agent and the oils of (2), (3) and (4) were mixed and heated (to 70° to 100° C.) for dissolution, thereby gelling the oils. Thereafter, the gelled oil was mixed with other additives as usual to obtain an oil foundation.

TABLE 2

| Appearance: | Inventive Product | Comparative Product |
|---|---|---|
| Oozing of oil | O | X |
| Crazing | O | Δ |
| Discoloration | O | X |

O: no
Δ: slight
X: yes

As will be seen from the above, the product of the invention does not allow oozing and crazing of the system in which liquid oils are contained in large amounts. In addition, because of the good dispersability of the pigments, discoloration does not take place.

EXAMPLE 3

Rouge:
The oil gelling agents used were aluminum tris(dicetyl phosphate) prepared in Reference 1 (inventive product) and dextrin palmitate (comparative product) to prepare rouges of the following formulation. These rouges were used for comparison with respect to the feel to the touch.

In this test, dextrin palmitate was used in an amount of 10% because gelling of liquid oils did not occur in an amount of 1 wt%.

Formulation:

| | | Inventive product | Comparative product |
|---|---|---|---|
| (1) | Gelling agent | 0.8% | 8.0% |
| (2) | Castor oil | 39.6 | 36.0 |
| (3) | Liquid paraffin | 35.64 | 32.4 |
| (4) | Lanolin | 3.96 | 3.6 |
| (5) | Beeswax | 5.0 | 5.0 |
| (6) | Candelilla wax | 3.2 | 3.2 |
| (7) | Carnauba wax | 3.0 | 3.0 |
| (8) | Titanium oxide | 2.0 | 2.0 |
| (9) | Red #202 | 1.3 | 1.3 |
| (10) | Red #204 | 2.2 | 2.2 |
| (11) | Red #227 AL lake | 2.5 | 2.5 |
| (12) | Orange #201 | 0.4 | 0.4 |
| (13) | Perfume | 0.4 | 0.4 |
| | Inventive product | Comparative product |
|---|---|---|
| Total | 100 | 100 |

Preparation:
The gelling agent and the oils of (2), (3) and (4) were mixed and heated for dissolution (70° C. for the inventive product and 90° C. for the comparative product) thereby gelling the oils, followed by mixing as usual to obtain a rouge.

The resulting rouges were subjected to a sensory test of 10 expert panelists. The results are shown in Table 3.

TABLE 3

| | Number of Favoring Panelists | | | |
|---|---|---|---|---|
| | Spreading | Gloss | Adherence | Fitness |
| Inventive Product | 8 | 10 | 8 | 10 |
| Comparative Product | 2 | 0 | 2 | 0 |

As will be seen from the above results, the cosmetic of the invention contains the gelling agent which permits the oils to gel in small amounts, so that the rouge has good spreadability and gloss of the liquid oils and is free of adherence with good fitness.

EXAMPLE 4

| | W/O type Moisture Cream: Formulation: | |
|---|---|---|
| (1) | Aluminum tris(dicetyl phosphate) obtained in Reference 1 | 0.1% |
| (2) | Vaseline | 6.0 |
| (3) | Cholesterol | 0.6 |
| (4) | Cetanol | 0.5 |
| (5) | Sorbitan sesqui-oleate | 2.0 |
| (6) | Liquid lanolin | 4.0 |
| (7) | Isopropyl palmitate | 8.0 |
| (8) | Squalane | 16.0 |
| (9) | Butylparaben | 0.1 |
| (10) | Methylparaben | 0.1 |
| (11) | Glycerin | 3.0 |
| (12) | Perfume | 0.2 |
| (13) | Purified water | balance |
| | Total | 100 |

Preparation:
The above ingredients were mixed as usual to obtain a W/O type cream. The cream had good emulsion stability and very good spreading without adherence.

Effects of the Invention:
The thus obtained cosmetics of the invention have better properties than known cosmetics with respect to oozing of oils, crazing, discoloration and the like. In addition, even when gelling agents are contained in low concentrations, good characteristic properties can be obtained. Thus, the cosmetics of the invention have such specific properties that the gelling agents do not influence the feel of cosmetic oils.

What is claimed is:
1. A method of preventing crazing or discoloration of a cosmetic, or oozing of oil therefrom, said cosmetic comprising at least one oil component selected from the group consisting of liquid paraffin, squalane, and an ester oil of an alcohol and a fatty acid: comprising adding to said cosmetic 0.1 to 30% of an oil gelling agent comprising at least one metal salt of a dialkyl phosphate of the following general formula (I), (II) or (III)

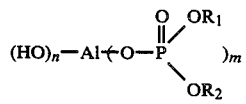 (I)

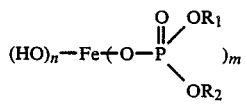 (II)

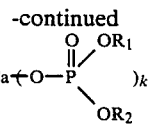 (III)

in which each $R_1$ and each $R_2$ independently represent a saturated or unsaturated, linear or branched hydrocarbon group having from 8 to 36 carbon atoms, m is as integer of from 1 to 3, n is an integer of from 0 to 2, k is a value of 1 or 2, and l is a value of 0 or 1.

2. The method of claim 1, wherein the metal salt of a dialkyl phosphate is the Al salt of formula (I).

3. The method of claim 1, wherein the metal salt of a dialkyl phosphate is the Fe salt of formula (II).

4. The method of claim 1, wherein the metal salt of a dialkyl phosphate is the Ca salt of formula (III).

* * * * *